United States Patent [19]

Porte

[11] Patent Number: 5,270,007

[45] Date of Patent: Dec. 14, 1993

[54] DOOR-MOUNTED WASH STATION

[75] Inventor: Johannes J. Porte, Webster, N.Y.

[73] Assignee: Eastman Kodak Company, Rochester, N.Y.

[21] Appl. No.: 990,149

[22] Filed: Dec. 14, 1992

[51] Int. Cl.$^5$ .................. G01N 35/00; G01N 35/06
[52] U.S. Cl. ........................ 422/64; 422/63; 436/49; 141/90
[58] Field of Search ............ 436/49, 180; 422/62, 422/64, 99, 100, 63; 141/90; 73/864.81, 864.24, 864.21

[56] References Cited

U.S. PATENT DOCUMENTS

| | | | |
|---|---|---|---|
| 3,266,322 | 8/1966 | Negersmith et al. | 73/864.22 |
| 3,677,091 | 7/1972 | Guigan | 73/864.22 |
| 3,719,086 | 3/1973 | Bannister et al. | 73/864.22 |
| 3,863,507 | 2/1975 | Jones et al. | 73/864.24 |
| 4,094,196 | 6/1978 | Friswell | 73/864.21 |
| 4,476,734 | 10/1984 | Banks et al. | 73/864.16 |
| 4,543,238 | 9/1985 | Mimura et al. | 422/63 |
| 4,820,497 | 4/1989 | Howell | 422/63 |
| 4,946,651 | 8/1990 | Liston et al. | 422/102 |
| 5,032,361 | 7/1991 | Kleinhappl et al. | 422/67 |
| 5,133,373 | 7/1992 | Hoffman et al. | 134/88 |

*Primary Examiner*—James C. Housel
*Assistant Examiner*—Robert Carpenter
*Attorney, Agent, or Firm*—Dana M. Schmidt

[57] ABSTRACT

An analyzer that uses a wash head to access via vertical movement a container in the analyzer for washing, and a soak reservoir to keep the wash head from crusting over. To eliminate the need for rotary motion of the wash head, a mechanism is provided for mounting the reservoir and for aligning it concentric with the vertical movement of the wash head, and for moving the reservoir out of alignment when the wash head needs to enter and wash a container.

5 Claims, 6 Drawing Sheets

DOOR-MOUNTED WASH STATION

FIELD OF THE INVENTION

The invention relates to an analyzer using a wash head for washing reaction containers in the analyzer, and especially to the construction of a soak reservoir used to keep the head from crusting over.

BACKGROUND OF THE INVENTION

Analyzers, particularly those involved with wet assays, conventionally require a washing station with a wash head to wash one or more containers used to carry out reactions. For example, in the Amerlite washer Model ZLE 202, a wash head is moved up and down into each of a series of containers arrayed on a moving platform, to aspirate out the incubated contents of each container and to wash the container several times. Because the wash head can use a solution of salts for the washing, it cannot be moved to a "home" position that exposes the head to the atmosphere. Otherwise, it is likely the head will crust over. Instead, it is commonly moved automatically into a soak reservoir to keep from drying out.

The problem with such an arrangement is that such varied positions for the wash head make it difficult to keep the movement of the head from deviating from a simple linear motion, e.g., down and up into and out of containers placed underneath the head. Although the soak reservoir can be just another position in the array of sample containers, the problem is that the contents of the soak reservoir need to be substantially larger than that of the sample containers, to avoid drying out the reservoir itself by evaporation. Furthermore, since the samples have to be removed after washing, such removal would also remove the soak reservoir.

On the other hand, it is more convenient to keep the motion of the wash head linear, if somehow the above-noted problems can be avoided.

Some attempts have been made in prior art analyzers to keep aspirators from departing from a linear up-and-down motion when they have to be cleaned (as opposed to being placed in a soak reservoir). However, typically the cleaning head undergoes a very complex disassembly and reassembly to move it away and back into alignment with the linear path of the aspirator. An example is shown in U.S. Pat. No. 4,820,497, which splits apart the cleaning head during its movement away. Such a construction is, of course, useless in the case of a soak reservoir that has to maintain a body of liquid.

SUMMARY OF THE INVENTION

I have designed a wash head soak reservoir in an analyzer that solves the above-noted problems.

More specifically, there is provided an analyzer for determining an analyte in a sample in a container, the analyzer comprising an incubator comprising a plurality of stations for holding containers with sample, first means for moving the stations through the incubator, a wash head mounted outside the incubator for washing a container inside the incubator, a movable door disposed between the wash head and the stations inside the incubator, means for translating the wash head in a linear path into and out of the incubator when the door is moved, and a soak reservoir for the wash head to keep the head from crusting over due to evaporation, the soak reservoir containing a continuously present liquid.

The analyzer is improved in that the analyzer further includes means for mounting the wash head soak reservoir aligned and concentric with the linear path of motion of the wash head, and second moving means for moving the mounting means and reservoir out of alignment with the path of motion when a container in the incubator is to be washed, so that the wash head can move through the previous position of the reservoir to wash a container and need not undergo rotational movement out of the path of motion.

Accordingly, it is an advantageous feature of the invention that access to a soak reservoir with liquid continually present can be had by the wash head without pivoting the latter out of its vertical path for accessing the container to be washed, and without splitting apart the soak reservoir.

Yet another advantageous feature of the invention is that such access by the wash head can be accomplished without raising the head all the way above the soak reservoir just to insert the wash head.

Other advantageous features will become apparent upon reference to the following Description of the Preferred Embodiments when read in light of the attached drawings.

DESCRIPTION OF THE PREFERRED EMBODIMENTS

The invention is hereinafter described in connection with the preferred embodiments, in which the incubator has several doors that cover access apertures for cuvette injection, patient sample injection, reagent injection, and for washing containers by a vertically moving wash head in an analyzer for a wet assay, the doors being opened and closed in a specific manner. In addition, the invention is useful regardless of the number of doors or rotors involved, to move the soak reservoir housing liquid continuously present, into and out of alignment with the vertical path of movement of the wash head.

As used herein, the term "continuously present" when applied to the liquid of the soak reservoir means that the liquid remains during the testing of a multiple number of samples, in contrast to those that may require replenishment after each sample is tested.

Figure 1:
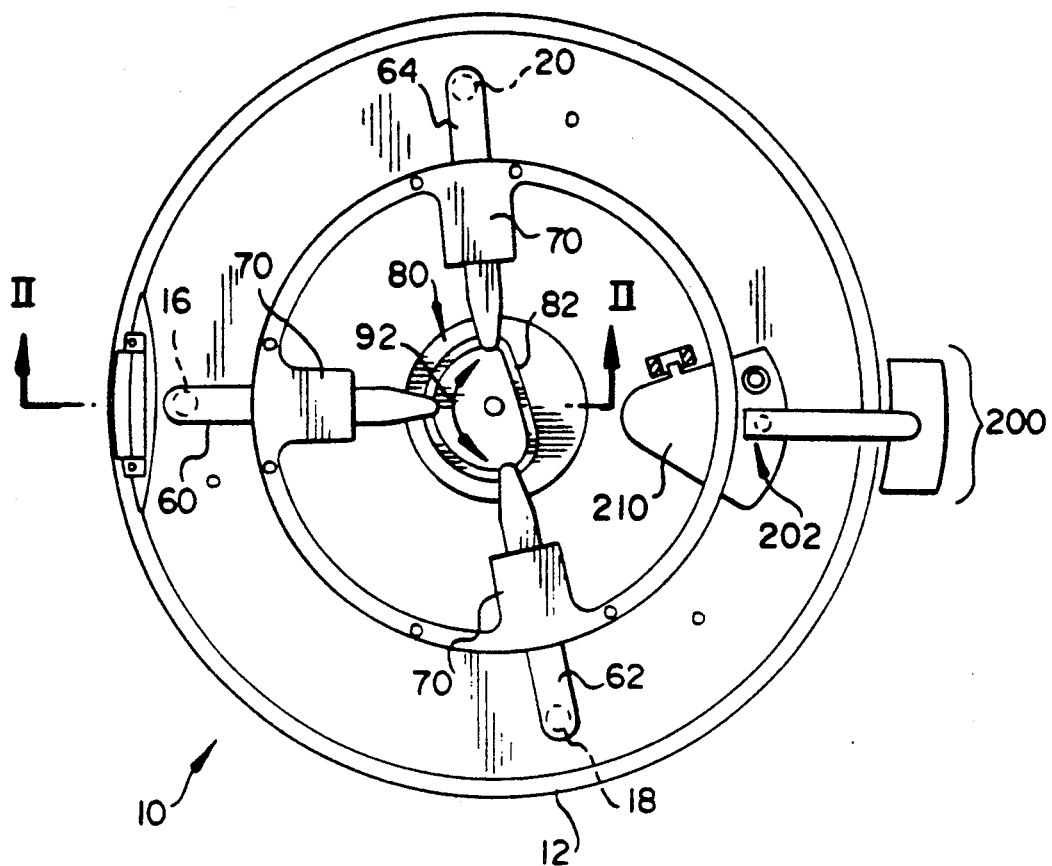
FIG. 1 is a plan view of an incubator housing, showing the soak reservoir constructed in accordance with the invention.
Figure 2:
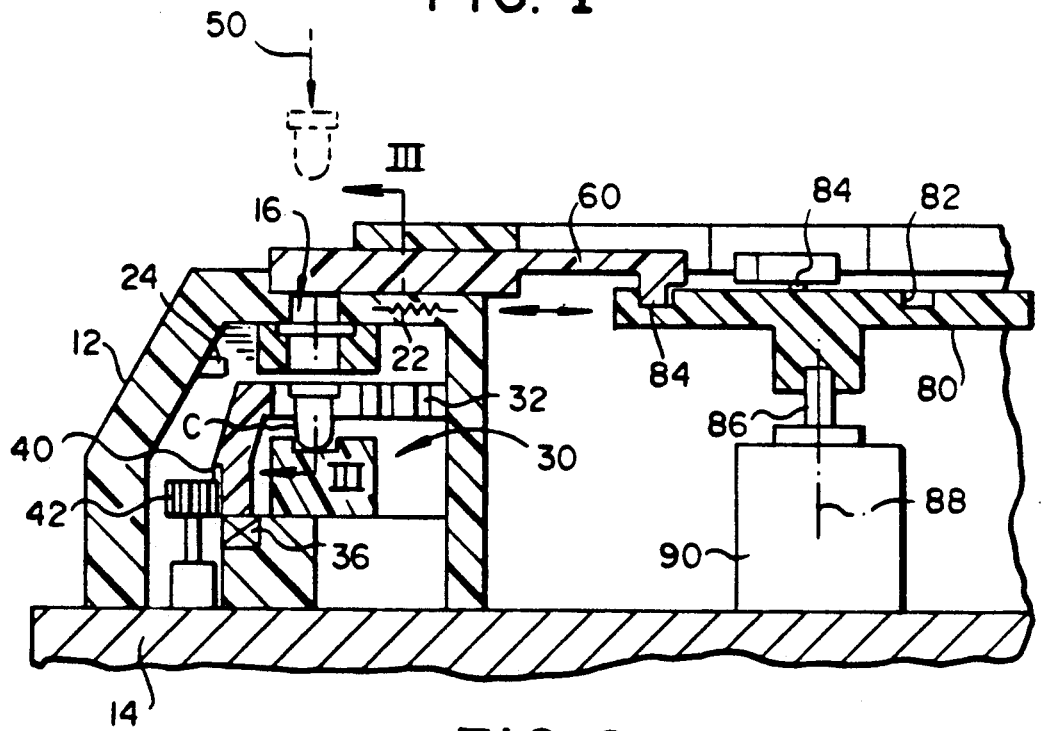
FIG. 2 is a fragmentary section view taken generally along the line II—II of FIG. 1.
Figure 3:
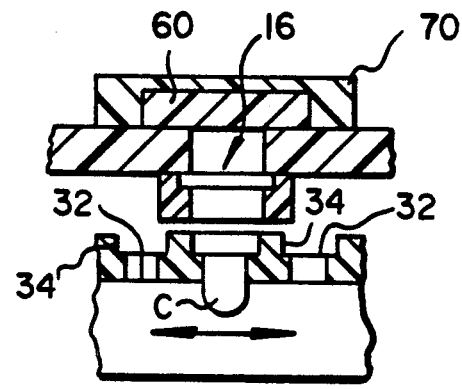
FIG. 3 is a fragmentary section view taken generally along the line III—III of FIG. 2.

As shown in FIGS. 1 and 2, a clinical analyzer in which the invention is useful preferably includes an incubator 10 comprising a housing 12 on a floor 14, FIG. 2, the housing having, as is conventional, several access apertures 16, 18 and 20, FIG. 1, preferably provided in the top surface of the incubator housing. (Alternatively they can be located elsewhere.) Also, as is conventional, incubator 10 includes heating elements 22, e.g., in the housing as shown in FIG. 2, or adjacent, and a temperature sensor, e.g., thermistor 24, to sense and control the temperature of the incubator, and a rotor 30 for holding patient sample and reagents for incubation. Preferably, the assay is a wet assay, so that rotor 30 has slots 32, FIG. 3, to accommodate cuvettes C on rails 34, the slots opening radially inwardly, FIG. 2, for example, to allow movement of cuvettes C off the rotor, by a mechanism not shown. Rotor 30 is mounted for rotation by an suitable mechanism, e.g., bearings 36, FIG. 2, a rack gear 40 being provided on the outside of the rotor for engagement by a drive mechanism, e.g., pinion gear 42 as shown (or a toothed belt drive).

Preferably, access aperture 16 is used to drop in individual containers or cuvettes "C", arrow 50, FIG. 2, whereas aperture 18 is used to add patient sample and aperture 20 to add reagent, in both cases by the use of two different aspirate and dispense devices (not shown and conventional). Each aperture is disposed so that it is vertically above where a container C is located by rotor 30. Each container preferably includes an antibody bound to an inside wall, specific to a targeted analyte. The washing done by wash head 202 (described below) removes unbound labeled antibody from this wall.

To help control the environment of incubator 10, a door 60, 62 and 64 is provided for each aperture 16, 18 and 20, FIG. 1, respectively. A separate door 210 provides access by wash head 202 as described hereinafter. Most preferably, doors 60, 62 and 64 are mounted for reciprocation in door frames 70, FIG. 3. Alternatively, other mechanisms can be used to slide the doors within a frame.

Figure 4:
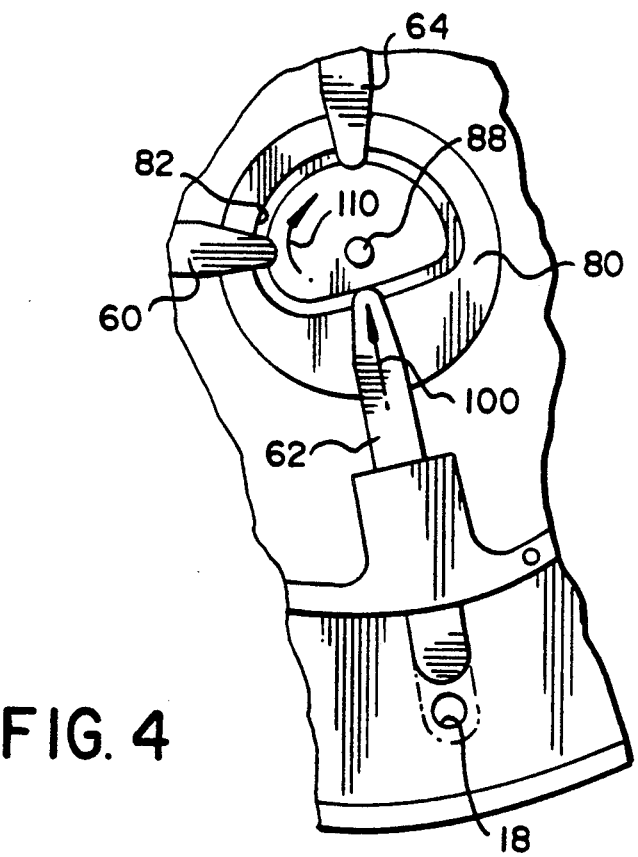
FIG. 4 is a fragmentary plan view similar to that of FIG. 1, showing one of the three cammed doors in its open position.

As described and claimed in commonly owned U.S. application Ser. No. 887,976, filed on May 22, 1992, by Johannes J. Porte, entitled "Cam-Operated Doors For An Incubator", the operation and control of any one door 60, 62 or 64, and preferably all of them together, is via a mechanical linkage comprising a cam 80, FIG. 1, having a cam track 82 and a cam follower 84 on each door that engages track 82, FIG. 2. Cam 80 is mounted on a drive shaft 86 that is preferably centered on the cam at its axis 88, and shaft 86 is in turn operated by a conventional motor 90 in accordance with commands from a computer (not shown). Because track 82 is eccentric with respect to axis 88, rotation of cam 80, arrow 92, FIG. 1, induces the doors to individually open and close by sliding within the frame. For example, when cam 80 is in the position shown in FIG. 4, only door 62 advances towards axis 88 so that aperture 18 is opened, arrow 100, to allow patient sample to be injected into a cuvette that is underneath aperture 18. Further rotation in the direction of arrow 110 will open door 60 while door 62 is open, and then door 62 shuts. Still further rotation opens door 64, and further rotation closes door 60. Finally, door 64 shuts when track 82 is back in the position shown in FIG. 1.

Figure 5:
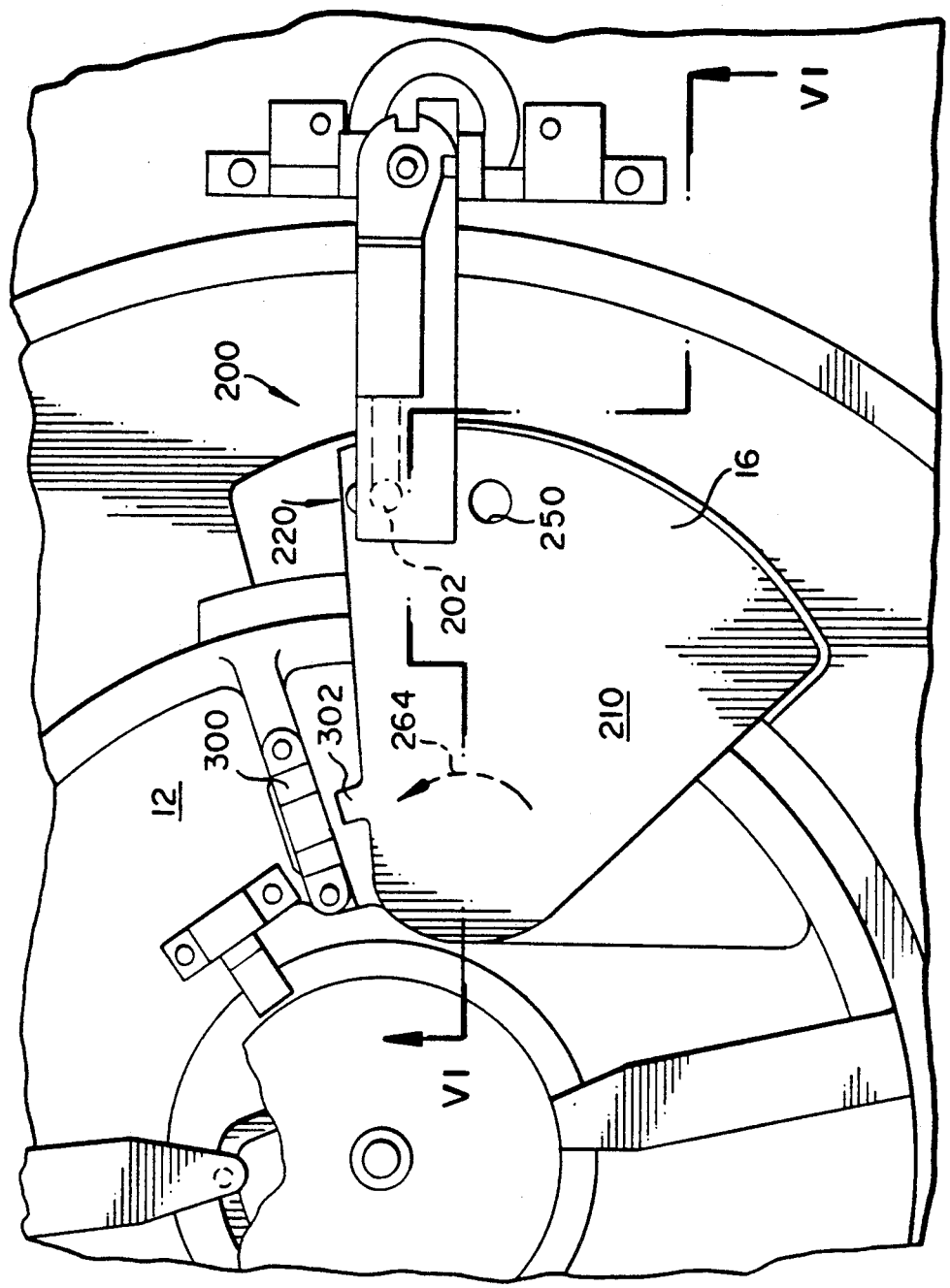
FIG. 5 is a fragmentary, enlarged plan view similar to FIG. 1, showing especially the door and wash head of the invention.
Figure 6:
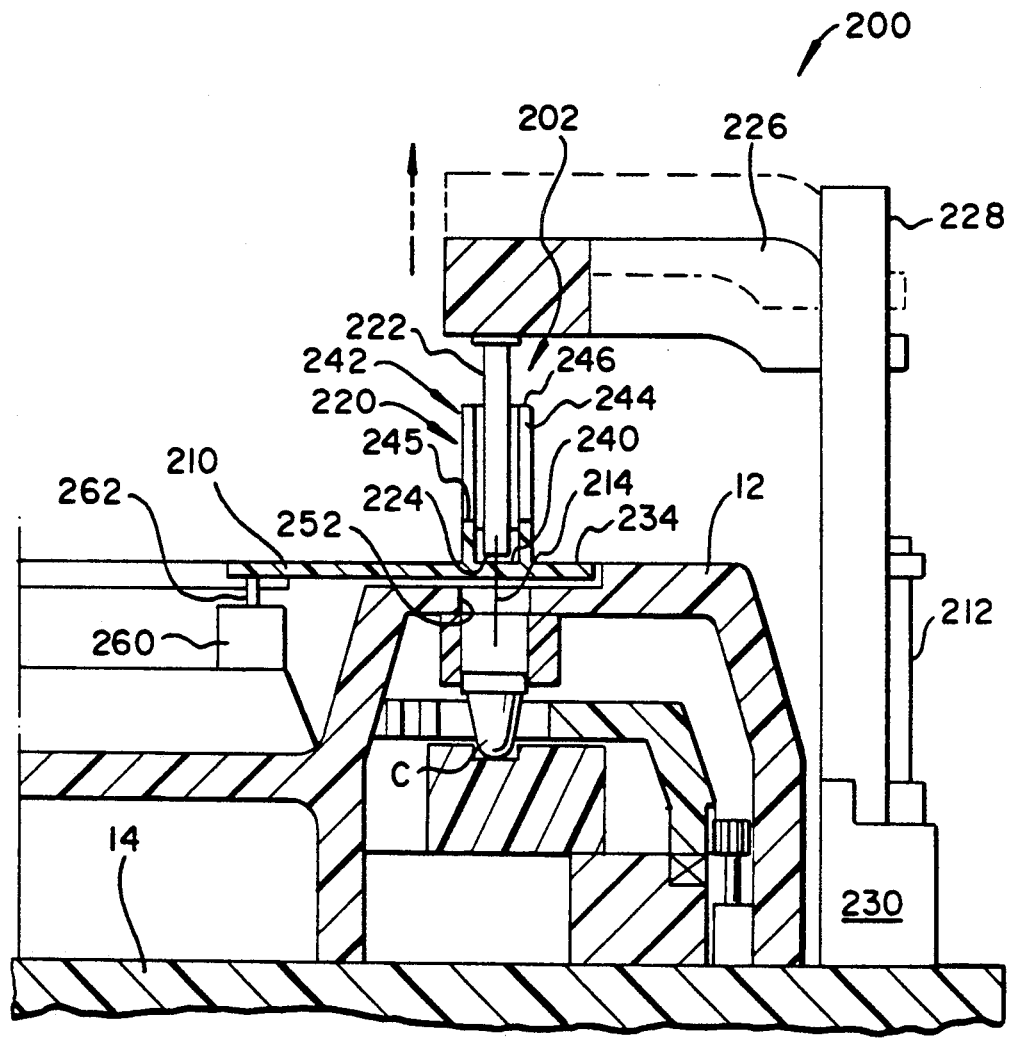
FIG. 6 is a fragmentary section view taken generally along the lines VI—VI of FIG. 5.

In accordance with the invention, washing of containers C is provided by a station 200, FIG. 5, comprising a wash head 202, FIG. 6, a door 210 providing access of wash head 202 to the containers, means 212 for translating the wash head in a linear path 214 down into a properly positioned container C, and a soak reservoir 220 mounted for movement into and out of path 214 to keep head 202 from crusting over. That is, head 202 preferably comprises, as is conventional, a nozzle 222 having an opening 224 at the bottom, the nozzle being connected via passageways (not shown) in an arm 226 mounted for vertical movement on a fixed stanchion 228. The vertical translating means 212 preferably features a conventional lead screw (in phantom) to raise and lower arm 226, operated by a motor 230. In this way, head 202 undergoes only vertical movement, within vertical path 214.

Soak reservoir 220 is mounted for movement into and out of path 214 by any suitable means. A preferred mechanism, FIGS. 5-8, is the mounting of the reservoir directly onto the upper surface 234 of door 210. Reservoir 220 preferably has a bottom wall 40, FIG. 6, and opposing sidewalls 242 such as is provided by a cylinder open at the top, sidewalls 242 also including a side opening 244, FIGS. 6 and 8, extending from horizontal shoulder 245 to top surface 246 of walls 242. The purpose of the side opening is to allow wash head 202 to access the reservoir by clearing only shoulder 245, instead of clearing top surface 246.

The access through housing 12 by wash head 202 occurs via an opening 250, FIG. 5, in door 210, and opening 252, FIG. 6, in housing 12.

A rotary solenoid 260 is provided for rotating door 210, which pivots above housing 12 about drive shaft 262.

The operation of the invention will be readily apparent from the preceding description. The "home" position of door 210 is that shown in FIGS. 5 and 6, with wash head 202 inserted into the continuously present wash liquid in soak reservoir 220. In this position, all apertures, such as aperture 252 in housing 12, are preferably covered by door 210 since aperture 250 is moved away from alignment with aperture 252.

Figure 7:
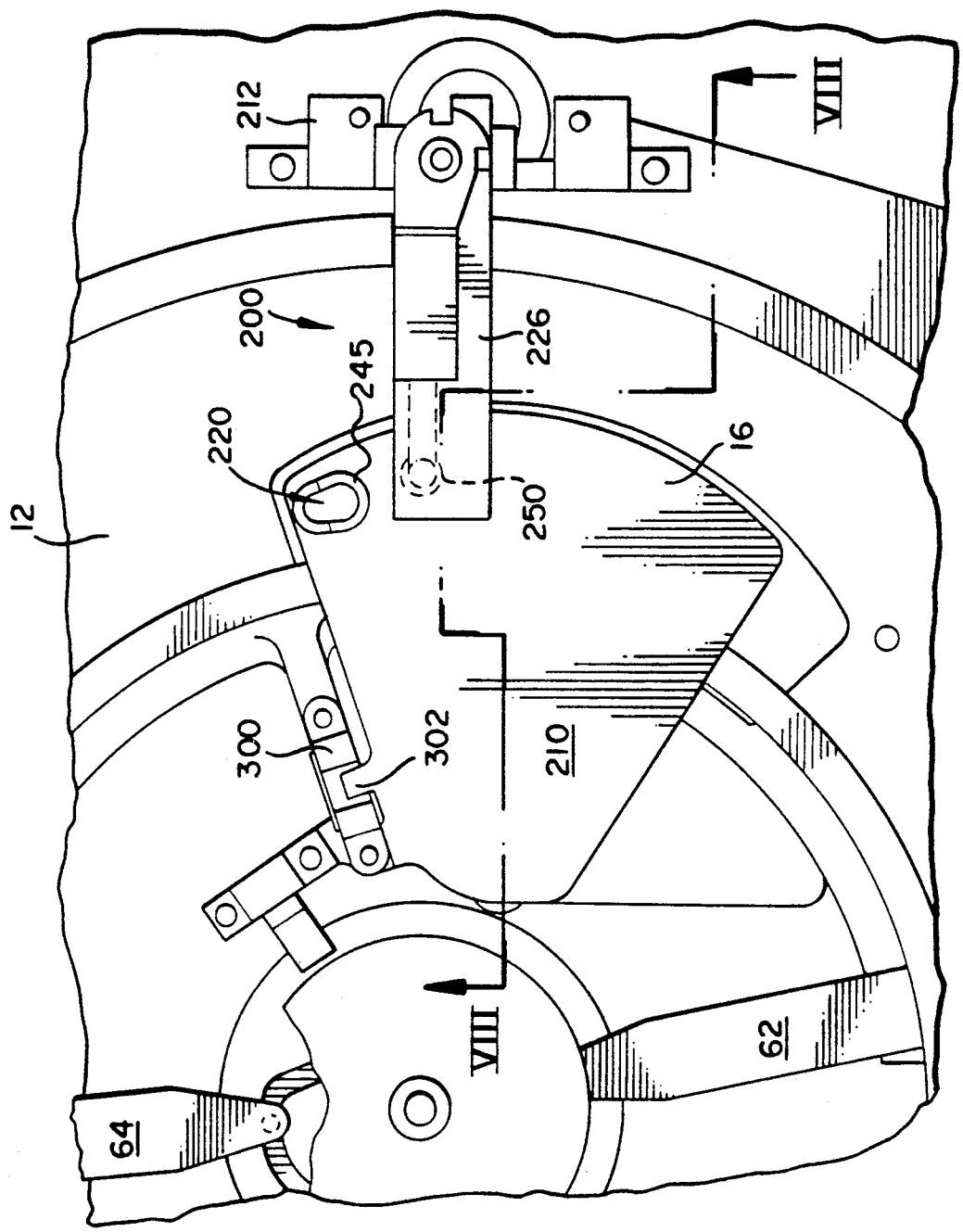
FIG. 7 is a fragmentary plan view similar to FIG. 5, but with the door in its other primary position.
Figure 8:
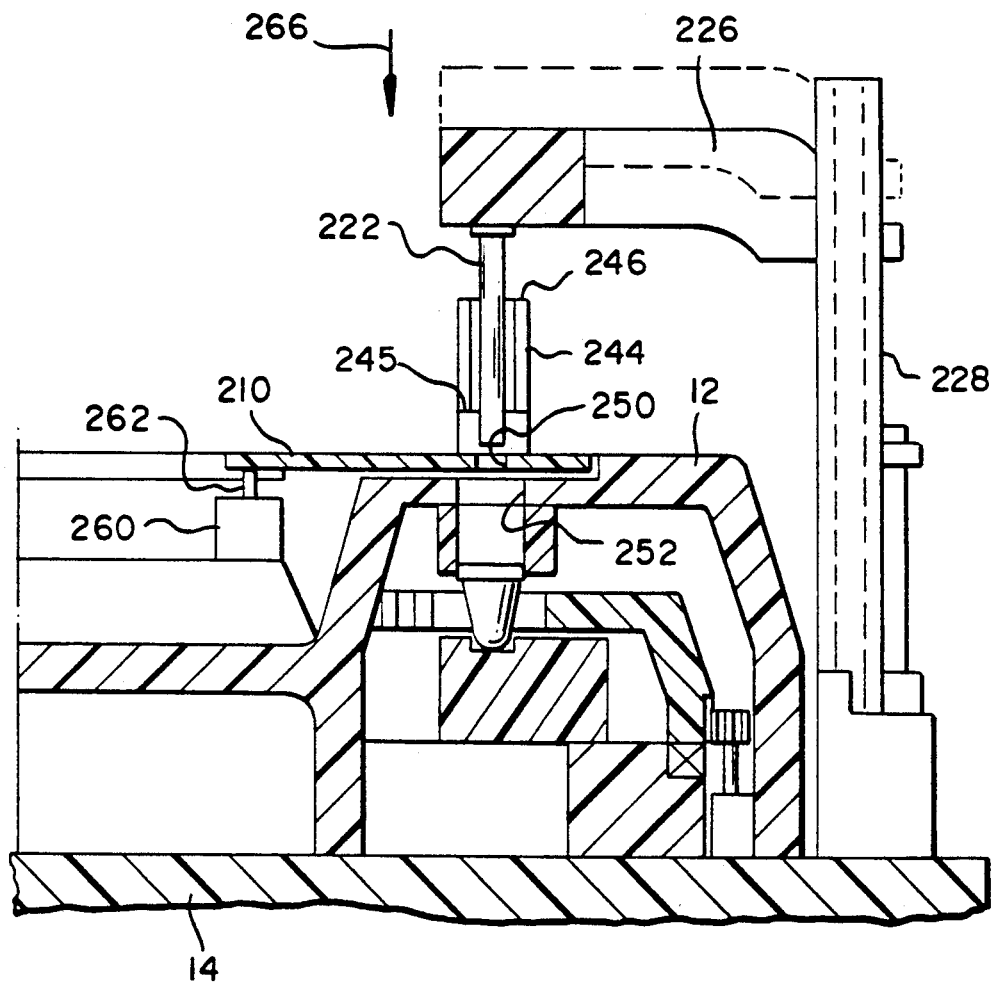
FIG. 8 is a section view taken generally along the line VIII—VIII of FIG. 7.

The other primary position of door 210 is shown in FIGS. 7 and 8. When wash head 202 is to penetrate housing 12 to wash a container, arm 226 is raised to the phantom position, FIGS. 6 and 8, in which head 202 vertically clears shoulder 245. Solenoid 260 is then activated to rotate door 210, arrow 264, FIG. 5, to move door 210 out of the soak position, and into the container access position shown in FIG. 7. Arm 226 is then lowered, arrow 266, FIG. 8 from its phantom position and beyond that shown in solid lines until nozzle 222 passes through apertures 250 and 252 and into a container C.

Optionally, an optical sensor 300, FIG. 7, can be included on housing 12, to sense the insertion of a flag 302 mounted on door 210, thus indicating that the door is open for head 202 to proceed downwardly through apertures 250 and 252.

As a further option, when wash head is inserted to wash a container, door 210 can either completely cover any other aperture through housing 12 into the incubator, or not if other dispensing devices need to access the incubator.

It is not necessary that soak reservoir 220 be mounted only on door 210. A separate pivoting mount above door 210 could be used (not shown), to move reservoir 220 into position slightly above the position shown on door 210, leaving door 210 to pivot solely for the purpose of aligning and misaligning openings 250 and 252 for access by wash head 202. That separate mount would be timed to cooperate with the movement of door 210.

All movements are controlled by a conventionally programmed computer, not shown.

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. In an analyzer for determining an analyte in a sample in a container, the analyzer comprising an incubator comprising a plurality of stations for holding containers with sample, first means for moving said stations through said incubator, a wash head mounted outside said incubator for washing a container inside said incubator, a movable door disposed between said wash head and said stations inside said incubator, means for translating said wash head in a linear path into and out of said incubator when said door is moved, and a wash head soak reservoir for said wash head to keep said head from crusting over due to evaporation, said soak reservoir containing a continuously present liquid;

the improvement wherein said wash head soak reservoir is mounted on said door and is capable of being aligned with said linear path of motion of said wash head at an alignment position, and further comprising second moving means for moving said door and reservoir into and out of alignment with said path of motion independent of said wash head for selective washing of said head and a container, so that said wash head need not undergo rotational movement out of said path of motion.

2. An analyzer as defined in claim 1, wherein said door is mounted to pivot about an axis that is generally parallel to said linear path of motion of said wash head.

3. An analyzer as defined in claim 2, wherein said second moving means comprises a rotary solenoid operatively connected to said door.

4. An analyzer as defined in claim 1, wherein said soak reservoir comprises a container of soaking liquid having a bottom wall, opposing sidewalls, and an opening adjacent to the top of one of said sidewalls for access to the liquid by said wash head.

5. An analyzer as defined in claim 4, wherein said opening is only in a portion of said one of said sidewalls and another of said sidewalls opposes said opening, so that said wash head can move through said sidewall portion to access said reservoir without having to vertically clear all of said sidewalls.

* * * * *